United States Patent [19]
Miklaus et al.

[11] Patent Number: 5,209,722
[45] Date of Patent: May 11, 1993

[54] ANKLE BRACE

[75] Inventors: Jeffry A. Miklaus, Mission Viejo; Richard J. Farr, Tustin; Kyle R. Tolly, Jr., Laguna Hills, all of Calif.

[73] Assignee: Joint Solutions, Inc., Tustin, Calif.

[21] Appl. No.: 858,274

[22] Filed: Mar. 26, 1992

[51] Int. Cl.⁵ .............................................. A61F 3/00
[52] U.S. Cl. .................................................... 602/27
[58] Field of Search .............. 602/27, 28, 29; 128/65, 128/80 F, 80 H

[56] References Cited

U.S. PATENT DOCUMENTS

| | | | |
|---|---|---|---|
| 4,280,489 | 7/1981 | Johnson, Jr. | 128/80 H |
| 4,510,927 | 4/1985 | Peters | 602/27 |
| 4,517,968 | 5/1985 | Green et al. | 602/27 |
| 4,934,355 | 6/1990 | Porcelli | 128/80 H |
| 4,938,777 | 7/1990 | Mason et al. | 128/80 H |
| 4,966,134 | 10/1990 | Brewer | 128/80 H |
| 5,031,607 | 7/1991 | Peters | 128/80 H |
| 5,094,232 | 3/1992 | Harris et al. | 602/27 X |

Primary Examiner—Richard J. Apley
Assistant Examiner—Beverly A. Meindl
Attorney, Agent, or Firm—Caesar, Rivise, Bernstein, Cohen & Pokotilow, Ltd.

[57] ABSTRACT

An ankle brace for a person. The brace basically comprises an elongate medial support member, an elongate lateral support member, four releasably securable straps for the support members, and a footpiece. Each of the support members is a semi-rigid plate configured to extend along and generally conform to the shape of a respective side of the leg of the wearer from a point just below the malleolus to a point substantially thereabove. Foam pads are provided on the support members to absorb shock and conform closely to the wearer's leg. The footpiece is also a semi-rigid member and comprises a base portion having a medial side and a lateral side and a pair of upstanding members projecting therefrom pivotally connected to respective ones of the support members adjacent the malleoli. The base portion includes a pad thereon and generally conforms to the bottom of the wearer's foot. A metatarsal pad is provided on the footpiece. The support members are connected to each other by the four straps. These straps extends through associated holes in the support members on the anterior side thereof and on the posterior side thereof to enable precise adjustment of the ankle brace. An elastic strap is arranged to be wrapped about the ankle brace in a "FIG. 8" configuration.

15 Claims, 3 Drawing Sheets

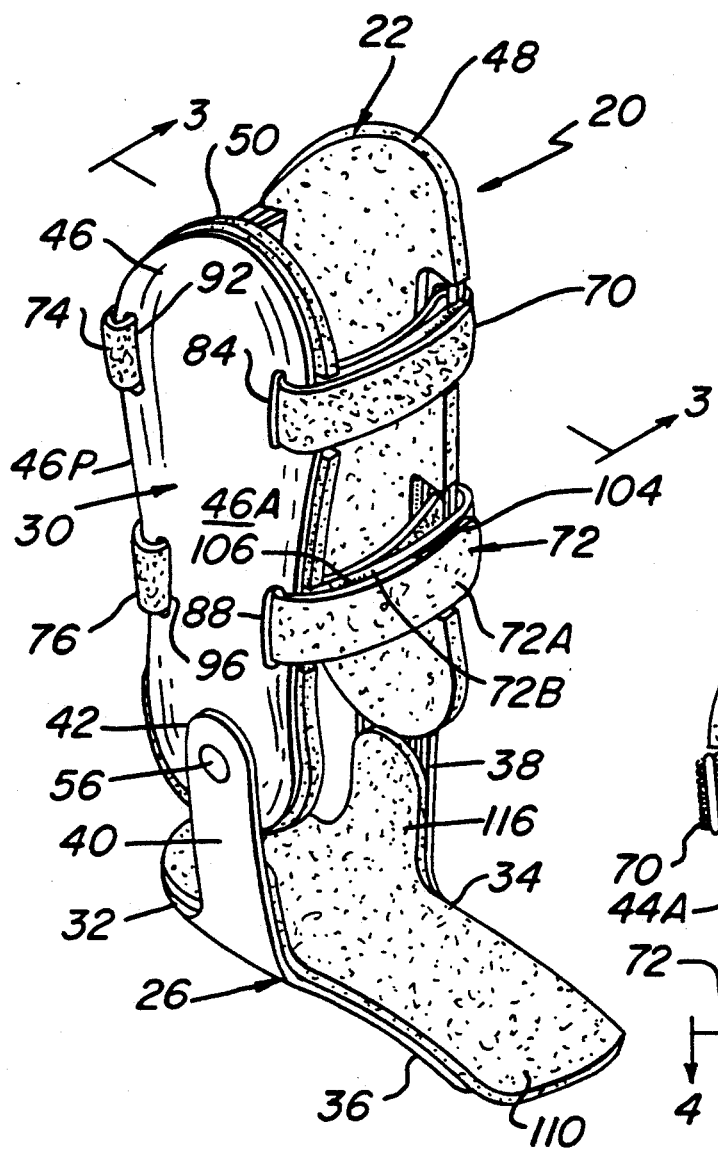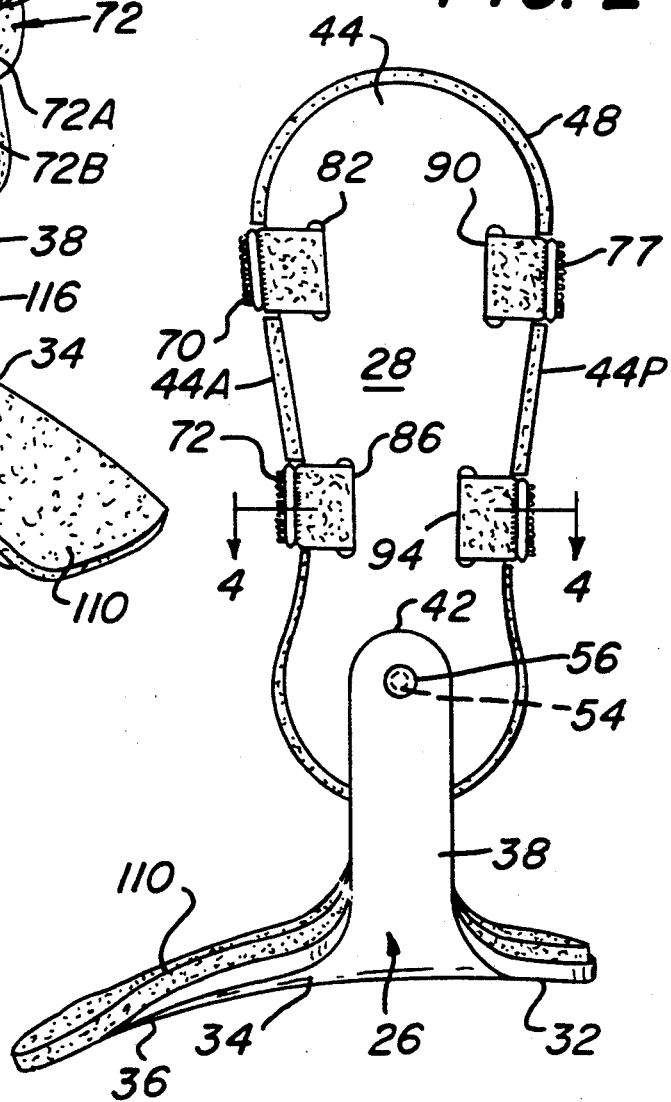

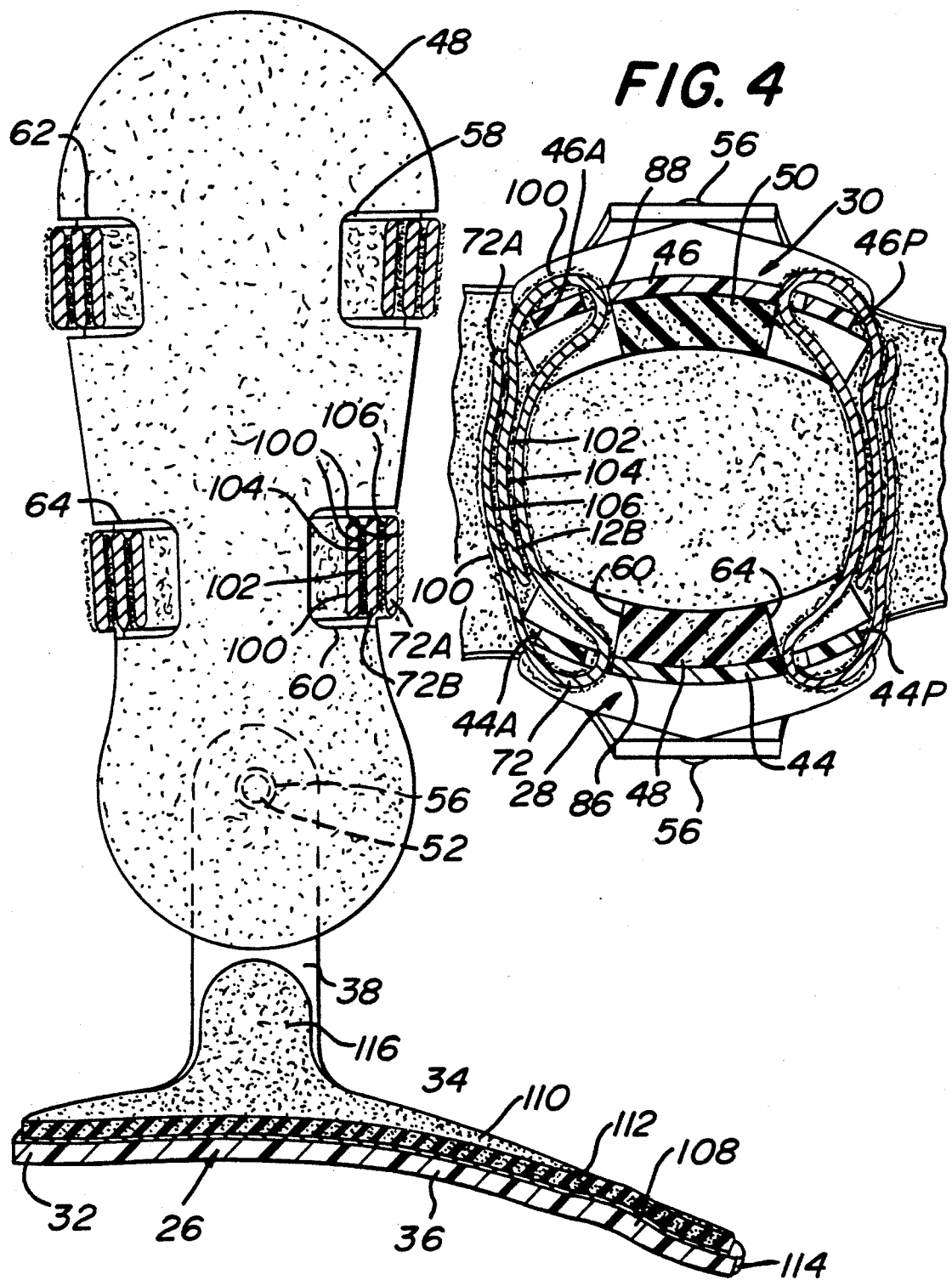

ANKLE BRACE

BACKGROUND OF THE INVENTION

The present invention generally relates to orthopedic devices and more particularly to ankle braces for protecting the ankle from inversion or eversion, while allowing near normal plantoflexion and dorsiflexion during use.

As is known a person's ankle may move in four different ways, namely, plantoflexion, dorsiflexion, inversion, and eversion. Dorsiflexion and plantoflexion constitute the up-down movement of the foot which normally occur during walking or running. Inversion and eversion are the inward and outward turning, respectively, of the ankle and are a frequent cause of ankle injury.

Various patents disclose braces for use on the ankle of a person to provide various benefits, e.g., support and/or to protect the ankle and/or promote the healing of an injured ankle, while enabling dorsiflexion and plantoflexion. Examples of such braces are: U.S. Pat. Nos. 4,280,489 (Johnson, Jr.), 4,510,927 (Peters), 4,934,355 (Porcelli), 4,938,777 (Mason et al.), 4,966,134 (Brewer), and 5,031,607 (Peters). While the aforementioned devices may be generally suitable for their intended purposes they nevertheless appear to leave something to be desired from one or more of the following standpoints, adequacy of support and/or stabilization provided, ability to permit normal plantoflexion and dorsiflexion during use, ease of application, comfort, and simplicity of construction.

Accordingly, a need exists for an ankle brace which overcomes the disadvantages of the prior art.

OBJECTS OF THE INVENTION

It is a general object of this invention to provide an ankle brace which overcomes the disadvantages of the prior art.

It is a further object of this invention to provide an ankle brace for protecting the ankle from inversion or eversion injury.

It is still a further object of this invention to provide an ankle brace for protecting the ankle from inversion or eversion injury, while allowing near normal plantoflexion and dorsiflexion during use.

It is yet a further object of this invention to provide an ankle brace which is easy to apply, conforms closely to the leg of the wearer, and is comfortable.

SUMMARY OF THE INVENTION

These and other objects of this invention are achieved by providing an ankle brace for a person wearing said brace. The ankle brace basically comprises an elongate medial support member, an elongate lateral support member, releasably securable connector means for the support members, and footpiece means. Each of the support members is substantially rigid, e.g., semi-rigid, and configured to extend along a respective side of the leg of the wearer from a point just below the malleolus to a point substantially thereabove. The footpiece is substantially rigid, e.g., is also formed of a semi-rigid material, and comprises a base portion having a medial side and a lateral side, and a pair of upstanding members projecting therefrom which are pivotally connected to respective ones of the support members adjacent the malleoli. The base portion generally conforms to the bottom of the wearer's foot.

The releasably securable means comprises a first strap connecting the medial support member to the lateral support member on the anterior side of the leg at a first height slightly above the malleoli, a second strap connecting the medial support member to the lateral support member on the anterior side of the leg at a second height adjacent the top of the support members, a third strap connecting the medial support member to the lateral support member on the posterior side of the leg at the first height, and a fourth strap connecting the medial support member to the lateral support member on the posterior side of the leg at the second height.

In accordance with a preferred embodiment of this invention each strap is arranged to form an adjustable size loop extending through associated holes in the support members to enable them to be readily adjusted to the wearer's leg. Moreover, each support member is configured to conform generally to the leg of the wearer and includes an inner surface having a shock absorbing pad thereon. The pad is arranged to closely conform to the leg of the wearer. The footpiece preferably includes a metatarsal pad portion.

DESCRIPTION OF THE DRAWING

Other objects and many attendant features of this invention will become readily appreciated as the same becomes better understood by reference to the following detailed description when considered in connection with the accompanying drawing wherein:

FIG. 1 is an isometric view of an ankle brace constructed in accordance with this invention;

FIG. 2 is an enlarged side elevational view of the ankle brace shown in FIG. 1;

FIG. 3 is an enlarged sectional view taken along line 3—3 of FIG. 1;

FIG. 4 is an enlarged sectional view taken along line 4—4 of FIG. 2;

DETAILED DESCRIPTION OF THE PREFERRED EMBODIMENT

Figure 5:
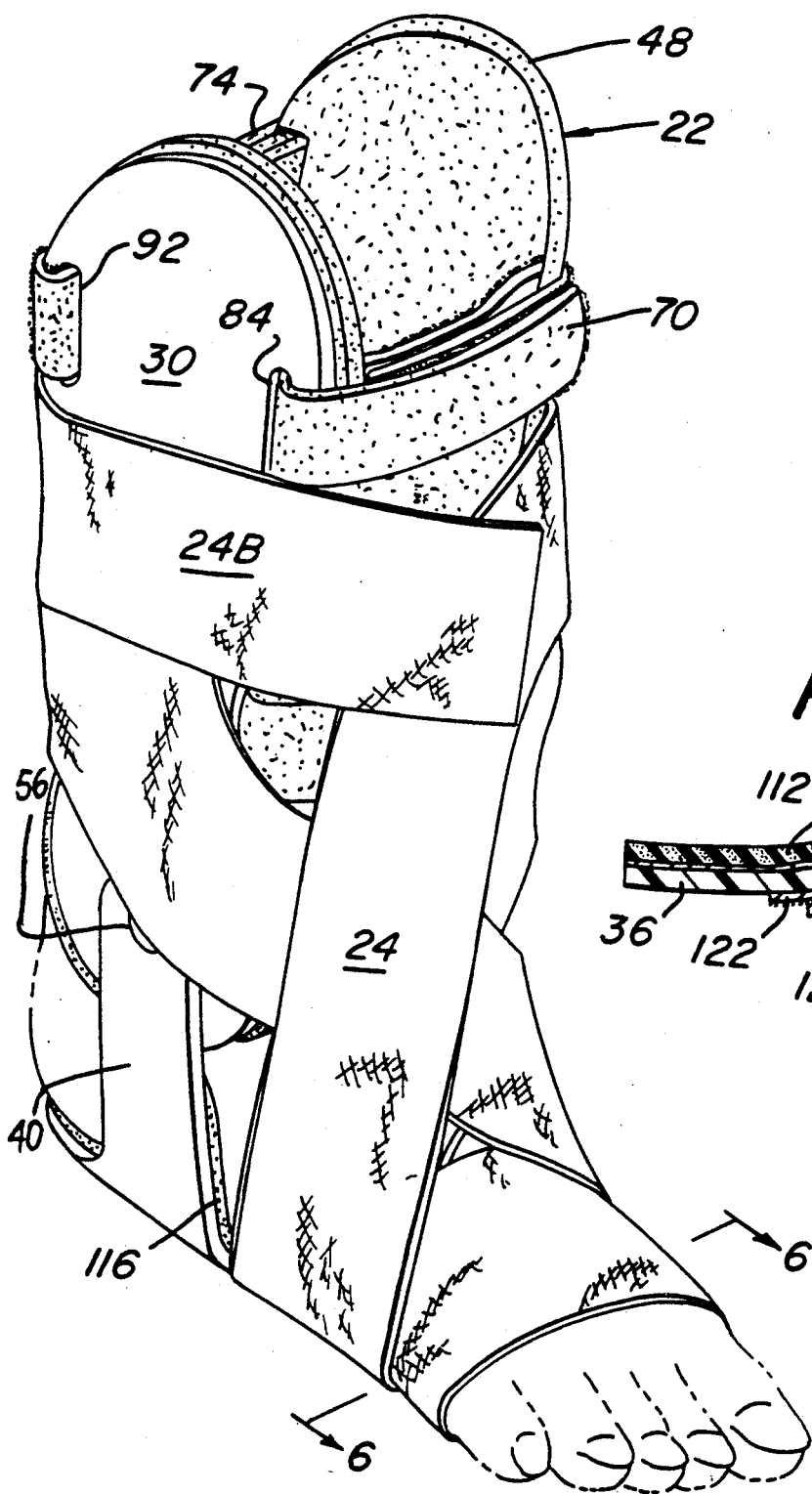
FIG. 5 is an isometric view of an ankle brace constructed in accordance with this invention shown in position on the ankle of a person.

Referring now to various figures of the drawing where like reference numerals refer to like parts, there is shown at 20 in FIG. 1, an ankle brace constructed in accordance with this invention. The ankle brace 20 is arranged to be worn on the lower leg, ankle and a portion of the foot of a person to minimize the possibility of an inversion or eversion injury to the ankle, while allowing near normal plantoflexion and dorsiflexion during use. As will be described in detail later braces constructed in accordance with this invention are arranged to closely conform to the wearer's leg and foot. Thus, a brace designed for use on the left foot is constructed as a mirror image of a brace designed for use on the right foot. In the interest of brevity only a right foot brace is shown and described herein, it being understood that the left foot brace is constructed in an identical manner, except for being a mirror image of the right foot brace.

The brace 20 basically comprises a frame assembly 22 and, if desired may optionally utilize a stabilizing strap 24. The frame assembly 22 by itself serves to provide sufficient support and stabilization for the ankle to achieve the results desired. However, in accordance with one preferred embodiment of the invention a stabilizing strap 24 in the form of an elastic web member (FIG. 5), to be described later, is secured to and wrapped about the frame assembly 22 after it is in place on the wearer's foot and ankle. The use of the strap 24, while not mandatory, never the less provides a greater degree of stability than the frame assembly 22 itself.

Referring to FIGS. 1-4 it can be seen that the frame assembly 22 basically comprises a footpiece 26, and a pair of side supports 28 and 30. Each of those components is formed of a substantially rigid, e.g., semi-rigid, material to provide the necessary support and stability. In the preferred embodiment of the invention that material is prosthetic grade polypropylene copolymer.

The footpiece is an integral member which is shaped to conform to the undersurface of the person's right or left foot (as the case may be) from the heel to a point beyond the metatarsal heads. Thus, the footpiece comprises a base in the form of a heel cup portion 32, arch support portion 34, a metatarsal support portion 36 including a metatarsal pad (to be described later), and a pair of uprights 38 and 40 projecting upward from the base. The arch support portion 34 of the footpiece serves to locate the subtalar joint of the wearer's foot in a neutral position and to aid in controlling subtalar motion. In addition, the arch support in combination with the metatarsal pad (to be described later) aligns the footpiece with respect to the wearer's sole to help keep the brace 20 in the desired proper anatomical position.

The uprights 38 and 40 extend upward from the medial and lateral sides, respectively, of the footpiece base adjacent the heel cup portion 32 and are in line with the natural medial and lateral pivot points, i.e., the malleoli, of the ankle. Each upright is an elongated member whose top end 42 is located above the malleolus on the side of the ankle at which that upright is located when the wearer's foot is supported on the footpiece base. The uprights serve as means for pivotally connecting the footpiece to respective ones of the side supports 28 and 30 at respective pivot points corresponding to the lateral malleolus and medial malleolus to permit normal, e.g., unhindered, flexion and extension.

Before describing that pivotable connection, a brief description of the side supports 28 and 30 is in order. To that end each side support is an elongated, padded shell arranged to be worn on a respective side of the wearer's leg. In accordance with a preferred embodiment of the invention the side supports 28 and 30 comprise shells 44 and 46, respectively, and associated pads or cushions 48 and 50. Each shell is molded of the same material as that of the footpiece so as to be semi-rigid. Moreover, each shell includes a concave inner surface which conforms generally to the anatomy of the wearer's leg over which the shell is disposed, e.g., it includes a recess portion adjacent its lower end which is anatomically modeled to accommodate the associated malleolus, and a recess portion to accommodate a portion of the side of the calf, etc. The cushion 48 is mounted on the inner surface of the medial shell 44 and the cushion 50 is mounted on the inner surface of the lateral shell 46.

Each shell has an anterior edge, designated by the reference identifier "A" and a posterior edge, designated by the reference identifier "P". When the shells 44 and 46 are in position on the leg the anterior edges 44A and 46A of the shells 44 and 46, respectively, are adjacent but spaced from each other along the anterior surface of the wearer's leg. In a similar manner the posterior edges 44P and 46P, of those shells are adjacent but spaced from each other along the posterior surface of the wearer's leg.

At the lower end of the medial shell 44 is a pivot hole 52 (FIG. 3) which is aligned with the pivot axis of the medial malleolus. A similar hole (not shown) is located at the lower end of the lateral shell aligned with the pivot axis of the lateral malleolus. The hole 52 in each shell cooperates with an associated upright of the footpiece to pivotally connect the footpiece to the side supports 28 and 30. To that end the medial upright 38 also includes a pivot hole 54 (FIG. 2) adjacent its top end and aligned with the pivot axis of the medial malleolus, while the lateral upright 40 includes a similar hole (not shown) aligned with the pivot axis of the lateral malleolus. The hole 52 in the medial side shell 44 and the hole 54 in the medial upright 38 are axially aligned and a pivot pin or rivet 56 extends therethrough. In a similar manner the holes 52 and 54 in the lateral side shell 46 and the lateral upright 38, respectively, are axially aligned and a pivot pin or rivet 56 extends through those holes. Each rivet 56 is preferably formed of a strong, corrosion resistent, biocompatible material, e.g., stainless steel.

Referring now to FIGS. 3 and 4 the details of the cushions or pads 48 and 50 will now be described. As can be seen therein each of the cushions 48 and 50 is slightly larger in size than the shell to which it is secured so that the periphery of the cushion extends or overhangs beyond the periphery of the shell. In the preferred embodiment of this invention the edge of the cushion extends approximately ⅛ inch (3.2 mm) beyond the periphery of the shell. This overhang ensures that when the brace is in place the peripheral edges of the shells do not dig into the wearer's leg. The cushion 48 includes a pair of spaced apart notches 58 and 60 in its anterior edge and a similar pair of notches 62 and 64 in its posterior edge. The notches are provided in the cushions to enable the releasably securable connector means (in the form of anterior and posterior straps—to be described hereinafter), to pass therethrough to hold the brace on the wearer's leg. The cushion 50 includes similar notches in its anterior and posterior edges.

In accordance with a preferred embodiment of this invention the pads 48 and 50 are ⅜ inch (9.5 mm) thick and are formed of a material, e.g., ergonomic urethane foam, having high energy absorption properties and which softens and conforms to the engaging portion of the wearer's leg by virtue of the natural heat generated from the leg portion. Moreover, the foam is preferably non-irritating to the skin of the wearer, and is sufficiently porous to aid in the dissipation of moisture away from the skin of the wearer. The pads are secured in place on the inner surface of their respective shells by any suitable means, e.g., an adhesive.

As just mentioned the side supports 28 and 30 are arranged to be, held in place on the wearer's leg by means of anterior and posterior straps. Those straps total four in number, with two of the straps, 70 and 72, comprising anterior straps and the other two, 74 and 76, forming posterior straps. The construction and use of the straps will be described later. Suffice it for now to state that the straps are coupled to respective portions of the side supports adjacent the anterior and posterior edges of those supports, and are separately adjustable. This arrangement enables the supports to be drawn into close proximity with each other so that they closely engage the wearer's leg over virtually their entire surface, irrespective of the contour of the leg and ankle.

Thus, the subject brace exhibits maximum adjustability, without any sacrifice in comfort, support and stability.

As can be seen in FIGS. 1-4 the anterior straps 70 and 72 are located between adjacent anterior edges the medial and lateral side supports 28 and 30 adjacent the top and bottom thereof, while the posterior straps 74 and 76 are similarly located between adjacent posterior edges of those supports. The means for mounting the straps in place on the side supports comprise plural slots in the side supports. In particular, an elongated, generally vertically oriented, slot 82 extends through the medial shell adjacent its anterior edge 44A near the top of the shell. A similar slot 84 extends through the lateral shell adjacent its anterior edge 46A near the top of the shell. The anterior strap 70 is arranged to be formed into a loop (as will be described later) to extend through the slots 82 and 84 to hold the anterior edges of the two shells close to each other at their top ends. Similar elongated, generally vertically oriented, slots 86 and 88 extend through the medial and lateral shells, respectively, adjacent their anterior edges near the bottom of those shells, with the anterior strap 72 formed into a loop extending through those slots to hold the lower anterior edges close to each other. The side supports 28 and 30 also include similar slots 90 and 92 adjacent their posterior edges 44P and 46P, respectively, at the top of those supports, and similar slots 94 and 96 adjacent their posterior edges at the bottom of those supports. The posterior strap 74 is arranged to be formed into a loop to extend through the slots 90 and 92 at the top of the side supports, while the posterior strap 76 is arranged to be formed into a loop to extend through the slots 94 and 96 at the bottom of those side supports.

As can be seen clearly in FIGS. 1 and 4 each of the straps 70, 72, 74, and 76 of the preferred embodiment of this invention consists of portions of releasably securable VELCRO hook and loop fastening components. Each of the straps is of identical construction so only one strap, namely, lower anterior strap 72, will be described. Thus, as can be seen the strap 72 comprises an elongated web having a pair of free ends 72A and 72B. The entire outer surface 100 of strap 72 is formed of the VELCRO loop component. The opposite or inner surface consists of a central portion 102 formed of the VELCRO loop component between pair of end portions 104 and 106 formed of the VELCRO hook component. The VELCRO component 104 is located on the free end 72A, while the VELCRO component 106 is located on the free end 72B. Accordingly when the strap 72 is formed into a loop, like that shown in FIG. 4, so that its free end 72A overlaps the free end 72B, the hook component 106 on the inner surface of the outer free end 72A engages and secures to the loop component 100 on the outer surface of the inner free end 72B. In addition, the hook component 104 on the inner free end 72B engages and secures to the loop 102 component on the inner surface of the strap between those ends so that the strap 72 is secured to itself between the anterior edges of the side supports.

As should be appreciated by those skilled in the art the amount of overlap of the free ends of the strap can be adjusted as desired, thereby enabling one to establish the desired spacing between the adjacent edges of the side supports to which the strap is connected. Thus, by utilizing the four separately adjustable straps, one can independently adjust the spacing between adjacent anterior edges and adjacent posterior edges at the top and bottom of the brace assembly. This provides significantly more adjustability than prior art braces which utilize one or more straps which extend fully about the circumference of the brace.

As mentioned earlier the footpiece 26 includes a metatarsal support portion 36 having a metatarsal pad. This pad is shown clearly in FIGS. 3 and 6 and basically comprises a convex projection 108 extending upward slightly from the surface of the footpiece portion 36 at the location of the metatarsal heads. The metatarsal pad 108 cooperates with the arch support to align the footpiece on the sole of the foot and help keep the brace in the proper anatomical position.

In the interests of comfort the footpiece includes a resilient cushion or pad 110, e.g., nylon covered neoprene, mounted on its upper surface. As can be seen in FIGS. 1-3 the pad 110 includes a base portion 112 which completely covers the base of the footpiece and extends a short distance, e.g., ½ inch (12.7 mm) past the anterior edge 114 of the footpiece base. The pad 110 also includes a pair of portions 116 extending upward, e.g., approximately 1 inch (25 mm) on respective ones of the uprights 38 and 40. The pad 110 is held in place by any suitable means, e.g., an adhesive.

Figure 6:
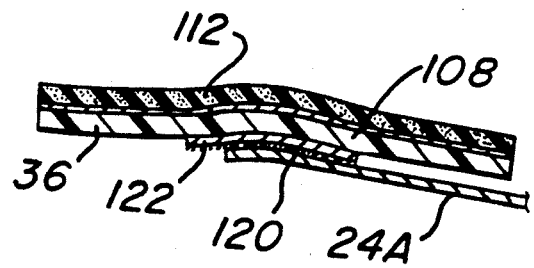
FIG. 6 is an enlarged sectional view taken along line 6—6 of FIG. 5.

Referring now to FIGS. 5 and 6, the details of the optional stabilizing strap 24 will be described. The strap basically comprises an elongated web of a semi-elastic bandage-like material which is arranged to be wrapped about the brace 22 after it is in place on the wearer's leg to provide additional stabilization. To that end the strap is wrapped about the brace in a conventional "FIG. 8" configuration. In order to expeditiously accomplish the wrapping of the strap about the brace, the strap includes a patch 120 (FIG. 6) of a VELCRO hook component secured to the inner surface at one end 24A of the strap 24. A patch 122 of a VELCRO loop component is secured, e.g, held by an adhesive, onto the underside of the footpiece 26. The strap is secured to the brace by engaging the patch 120 which is mounted on the strap 24 onto the patch 122 On the bottom of the footpiece. The strap 24 can then be wrapped about the footpiece and the foot as shown in FIG. 6, to further secure the metatarsals to the footpiece. The wrap is continued into the FIG. 8 pattern extending up the brace, thereby increasing the stabilization. The free end 24 of the strap is secured in place by means of patches (not shown) of VELCRO hook components which are located near the top of the medial and lateral side supports 28 and 30, respectively, and which releasably engage the material making up the strap 24 adjacent its free end portion 24B.

Without further elaboration the foregoing will so fully illustrate our invention that others may, by applying current or future knowledge, adapt the same for use under various conditions of service.

We claim:

1. An ankle brace for a person, said brace comprising an elongate medial support member, an elongate lateral support member, releasably securable connector means for said support members, and footpiece means, each of said support members being substantially rigid and configured to extend along a respective side of the leg of the person from a point just below the malleolus to a point substantially thereabove, said footpiece means comprising a base portion having a medial side and a lateral side and a pair of upstanding members projecting therefrom and pivotally connected to respective ones of said support members adjacent said malleoli, said base portion being substantially rigid and generally conforming to the bottom of the foot of the person, said releasably securable means comprising a first strap connecting the medial support member to the lateral support member only on the anterior side of the leg of the person at a first height slightly above the malleoli, a second strap connecting the medial support member to the lateral support member only on the anterior side of the leg of the person at a second height adjacent the top of said support members, a third strap connecting the medial support member to the lateral support member only on the posterior side of the leg of the person at said first height, and a fourth strap connecting the medial support member to the lateral support member only on the posterior side of the leg of the person at said second height.

2. The ankle brace of claim 1 wherein each of said support members includes an anterior portion, a posterior portion, and a first opening at said first height adjacent said anterior portion, a second opening at said second height adjacent said anterior portion, a third opening at said first height adjacent said posterior portion, and a fourth opening at said second height adjacent said posterior portion, and wherein said first strap only extends through said first openings in said support members, said second strap only extends through said second openings in said support members, said third strap only extends through said third openings in said support members, and said fourth strap only extends through said fourth openings in said support members.

3. The ankle brace of claim 2 wherein each of said straps is arranged to be releasably secured to itself to form a loop of adjustable size, said loop extending through said associated openings in said support members.

4. The ankle brace of claim 3 wherein each of said straps comprises an inner surface and an outer surface, and wherein portions of said inner surface are arranged to be releasably secured to each other between their respective openings, and wherein portions of said outer surface are arranged to be releasably secured to each other.

5. The ankle brace of claim 1 wherein said medial support member conforms generally to the medial side of the leg of the person, and said lateral support member conforms generally to the lateral side of the leg of the person.

6. The ankle brace of claim 5 wherein each of said support members and said footpiece is formed of a semi-rigid material.

7. The ankle brace of claim 5 wherein each of said support members includes an inner surface and wherein said ankle brace additionally comprises padding means located on the inner surface of each of said support members.

8. The ankle brace of claim 7 wherein said padding means extends slightly beyond the periphery of each of said support members.

9. The ankle brace of claim 7 wherein each of said padding means comprises a foam.

10. The ankle brace of claim 9 wherein said foam is arranged to soften and conform to the shape of the engaging portion of the person by virtue of the natural body heat generated by the person.

11. An ankle brace for a person, said brace comprising an elongate medial support member, an elongate lateral support member, releasably securable connector means for said support members, and a footpiece, each of said support members being substantially rigid and configured to extend along a respective side of the leg of the person from a point just below the malleolus to a point substantially thereabove, said footpiece comprising a base portion having a medial side and a lateral side and a pair of upstanding members projecting therefrom and pivotally connected to respective ones of said support members adjacent said malleoli, said base portion of said footpiece extending from the heel of the foot of the person to beyond the metatarsal heads of the foot of the person, said base portion being substantially rigid and generally conforming to the bottom of the foot of the person, said releasably securable means comprising a first strap connecting the medial support member to the lateral support member on the anterior side of the leg of the person at a first height slightly above the malleoli, a second strap connecting the medial support member to the lateral support member on the anterior side of the leg of the person at a second height adjacent the top of said support members, a third strap connecting the medial support member to the lateral support member on the posterior side of the leg of the person at said first height, and a fourth strap connecting the medial support member to the lateral support member on the posterior side of the leg of the person at said second height.

12. The ankle brace of claim 11 wherein said footpiece includes a convex portion projecting slightly upward from said base portion adjacent the metatarsal heads of the foot of the person.

13. The ankle brace of claim 11 additionally comprising padding means secured to said footpiece.

14. The ankle brace of claim 13 wherein said padding means extends beyond the anterior edge of said footpiece.

15. The ankle brace of claim 1 comprising an elastic material strap arranged to be wrapped about and releasably secured to said brace.

* * * * *